United States Patent
Kamiya et al.

(10) Patent No.: US 10,410,851 B2
(45) Date of Patent: Sep. 10, 2019

(54) MATRIX-ASSISTED LASER DESORPTION MASS SPECTROMETRY OF HIGH MOLECULAR WEIGHT POLYOXYETHYLENE DERIVATIVE

(71) Applicant: NOF CORPORATION, Tokyo (JP)

(72) Inventors: Masaki Kamiya, Kawasaki (JP); Ryota Matsuki, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/559,540

(22) PCT Filed: Mar. 30, 2016

(86) PCT No.: PCT/JP2016/060387
§ 371 (c)(1),
(2) Date: Sep. 19, 2017

(87) PCT Pub. No.: WO2016/159074
PCT Pub. Date: Oct. 6, 2016

(65) Prior Publication Data
US 2018/0096831 A1    Apr. 5, 2018

(30) Foreign Application Priority Data

Mar. 31, 2015   (JP) ................................ 2015-071739

(51) Int. Cl.
*G01N 27/64*   (2006.01)
*G01N 33/68*   (2006.01)
(Continued)

(52) U.S. Cl.
CPC ............ *H01J 49/164* (2013.01); *G01N 27/64* (2013.01); *G01N 33/6851* (2013.01); *H01J 49/0418* (2013.01)

(58) Field of Classification Search
CPC .......... H01J 49/164; H01J 49/26; H01J 49/00; H01J 49/0418; G01N 27/64; G01N 33/6851
(Continued)

(56) References Cited

U.S. PATENT DOCUMENTS

2009/0045332 A1    2/2009  Yoshimura et al.
2015/0076340 A1*   3/2015  Liang ................... H01J 49/164
                                                          250/282

FOREIGN PATENT DOCUMENTS

CN         1773275 A      5/2006
CN       101329301 A     12/2008
(Continued)

OTHER PUBLICATIONS

International Search Report dated Jun. 21, 2016 issued by the International Searching Authority in counterpart International Application No. PCT/JP2016/060387.
(Continued)

*Primary Examiner* — Nicole M Ippolito
*Assistant Examiner* — Hanway Chang
(74) *Attorney, Agent, or Firm* — Sughrue Mion, PLLC (57) ABSTRACT

A matrix-assisted laser desorption (MALDI) mass spectrometry in which a mixture comprising a polyethylene glycol derivative having a molecular weight of 40,000 or more and a matrix is irradiated with laser beam to vaporize the polyethylene glycol derivative together with the matrix, thereby measuring a molecular weight of the polyethylene glycol derivative, wherein as the matrix, a low polar matrix having a 1-octanol/water partition coefficient (logPow) of 4.1 to 4.8 is used. Also disclosed is a matrix for use in the matrix-assisted laser desorption (MALDI) mass spectrometry.

6 Claims, 9 Drawing Sheets

MASS SPECTRUM OF EXAMPLE 1

(51) Int. Cl.
 H01J 49/04 (2006.01)
 H01J 49/16 (2006.01)
(58) Field of Classification Search
 USPC ........................................ 250/281, 282, 288
 See application file for complete search history.

(56) References Cited

FOREIGN PATENT DOCUMENTS

| CN | 101710097 A | 5/2010 |
|---|---|---|
| CN | 102603707 A | 7/2012 |
| JP | 2012-122761 A | 6/2012 |
| WO | 2014/022501 A2 | 2/2014 |
| WO | 2014/139602 A1 | 9/2014 |
| WO | 2014/188344 A1 | 11/2014 |

OTHER PUBLICATIONS

S.D. Hanton; "Mass Spectrometry of Polymers and Polymer Surfaces"; Chemical Reviews; 2001; vol. 101; No. 2; pp. 527-569; 44 pgs. total.

Michel W.F. Nielen; "MALDI Time-of-Flight Mass Spectrometry of Synthetic Polymers"; Mass Spectrometry Reviews; 1999; vol. 18; pp. 309-344; 36 pgs. total.

Andrew J. Hoteling et al; "Exploring the Importance of the Relative Solubility of Matrix and Analyte in MALDI Sample Preparation Using HPLC"; Analytical Chemistry; Sep. 1, 2004; vol. 76; No. 17; pp. 5157-5164; 8 pgs. total.

Heike Brandt et al; "Investigating the Effect of Mixing Ratio on Molar Mass Distributions of Synthetic Polymers determined by MALDI-TOF Mass Spectrometry using Design of Experiments"; Journal of the American Society for Mass Spectrometry; 2010; vol. 21; pp. 1870-1875; 6 pgs. total.

De Miguel, et al., "Poly(y-benzyl-L-glutamate)-PEG-alendronate multivalent nanoparticles for bone targeting", 2014, International Journal of Pharmaceutics, vol. 460, Issue No. 1, pp. 73-82, XP 028548414.

Lou, et al., "A pitfall of using 2-[(2E)-3-(4-tert-butylphenyl)-2-methylprop-2-enylidene]malononitrile as a matrix in MALDI TOF MS: chemical adduction of matrix to analyte amino groups" 2010, Journal of Mass Spectrometry, vol. 45, Issue No. 10, pp. 1195-1202, XP 055503597.

Meier, et al., "Integration of MALDI-TOFMS as high-throughput screening tool into the workflow of combinatorial polymer research", 2005, Review of Scientific Instruments, vol. 76, Issue No. 6, 5 pages total, XP 012079437.

Communication dated Sep. 10, 2018, issued by the European Patent Office in counterpart European Patent Application No. 16772955.7.

Communication dated Jun. 25, 2019, from China National Intellectual Property Administration in corresponding Chinese Application No. 201680019749.8.

\* cited by examiner

FIG. 1

MASS SPECTRUM OF EXAMPLE 1

FIG. 2

MASS SPECTRUM OF COMPARATIVE EXAMPLE 1-1

FIG. 3

MASS SPECTRUM OF COMPARATIVE EXAMPLE 1-2

FIG. 4

MASS SPECTRUM OF EXAMPLE 2

FIG. 5

MASS SPECTRUM OF COMPARATIVE EXAMPLE 2-1

FIG. 6

MASS SPECTRUM OF COMPARATIVE EXAMPLE 2-2

FIG. 7

MASS SPECTRUM OF EXAMPLE 3

FIG. 8

MASS SPECTRUM OF COMPARATIVE EXAMPLE 3-1

FIG. 9

MASS SPECTRUM OF COMPARATIVE EXAMPLE 3-2

FIG. 10

MASS SPECTRUM OF EXAMPLE 4

FIG. 11

MASS SPECTRUM OF COMPARATIVE EXAMPLE 4-1

FIG. 12

MASS SPECTRUM OF COMPARATIVE EXAMPLE 4-2

FIG. 13

MASS SPECTRUM OF EXAMPLE 5

FIG. 14

MASS SPECTRUM OF COMPARATIVE EXAMPLE 5-1

FIG. 15

MASS SPECTRUM OF COMPARATIVE EXAMPLE 5-2

FIG. 16

MASS SPECTRUM OF EXAMPLE 6

FIG. 17

MASS SPECTRUM OF COMPARATIVE EXAMPLE 6-1

FIG. 18

MASS SPECTRUM OF COMPARATIVE EXAMPLE 6-2

MATRIX-ASSISTED LASER DESORPTION MASS SPECTROMETRY OF HIGH MOLECULAR WEIGHT POLYOXYETHYLENE DERIVATIVE

TECHNICAL FIELD

The present invention relates to matrix-assisted laser desorption (hereinafter referred to as MALDI) mass spectrometry of a high molecular weight polyethylene glycol derivative.

BACKGROUND ART

The MALDI mass spectrometry is an analytical method in which a mixture of a matrix and a polymer is irradiated with laser beam to vaporize and ionize the polymer together with the matrix, thereby measuring a molecular weight of the polymer. A role of the matrix in the MALDI mass spectrometry includes to transmit energy of the laser beam to the polymer, thereby ionizing the polymer. Therefore, affinity between the matrix and the polymer is important. As a guide of the affinity, it has been recommended to use a highly polar matrix, for example, α-cyano-4-hydroxycinnamic acid (CHCA) or 2,5-dihydroxybenzoic acid (DHB) for the measurement of a highly polar polymer, for example, polyethylene glycol (PEG). Further, it has been recommended to use a low polar matrix, for example, dithranol or retinoic acid (RA) for the measurement of a low polar polymer, for example, polystyrene (PS) (Non-Patent Documents 1 and 2). Moreover, it has been reported that in the MALDI mass spectrometry of polyethylene glycol having a molecular weight of 10,000, CHCA which is the highly polar matrix is the best (Non-Patent Document 3).

On the other hand, it is generally known that the measurement of a high molecular weight polymer by the MALDI mass spectrometry is difficult. This is because that since the ionization becomes difficult with increase in a molecular weight, it is necessary to increase the laser intensity irradiated, but decomposition of the polymer molecule by the laser irradiation tends to occur. Therefore, by way of example, in the case of polyethylene glycol, only the measurement results for the polyethylene glycols having a molecular weight of 25,000 or less are reported (Non-Patent Document 2).

PRIOR ART DOCUMENT

Non-Patent Document

Non-Patent Document 1: Chemical Reviews, 2001, vol. 101, pp 527-569
Non-Patent Document 2: Mass Spectrometry Reviews, 1999, vol. 18, pp 309-344
Non-Patent Document 3: Analytical Chemistry, 2004, vol. 76, pp 5157-5164

SUMMARY OF THE INVENTION

Problems that the Invention is to Solve

As described above, a molecular weight of the high molecular weight polyethylene glycol derivative is difficult to measure by the MALDI mass spectrometry. Further, in particular, in the case of a polymer having a branched structure, decomposition by the laser irradiation is remarkably observed and signal intensity is not sufficient in many cases. Therefore, it is desired to be able to measure the molecular weight of the high molecular weight polyethylene glycol derivative by MALDI mass spectrometry.

An object of the present invention is to be able to obtain a signal having higher intensity than heretofore in the MALDI mass spectrometry of the high molecular weight polyethylene glycol derivative.

Means for Solving the Problems

The present invention includes the following items.
(1) A matrix-assisted laser desorption mass spectrometry in which a mixture comprising a polyethylene glycol derivative having a molecular weight of 40,000 or more and a matrix is irradiated with laser beam to vaporize the polyethylene glycol derivative together with the matrix, thereby measuring a molecular weight of the polyethylene glycol derivative, wherein as the matrix, a low polar matrix having a 1-octanol/water partition coefficient (logPow) of 4.1 to 4.8 is used.
(2) The matrix-assisted laser desorption mass spectrometry as described in (1), wherein a molecular weight of the polyethylene glycol derivative is 60,000 or more.
(3) The matrix-assisted laser desorption mass spectrometry as described in (1) or (2), wherein the matrix is trans-2-[3-(4-tert-butylphenyl)-2-methyl-2-propenylidene]malononitrile.
(4) A matrix for use in a matrix-assisted laser desorption mass spectrometry of a polyethylene glycol derivative having a molecular weight of 40,000 or more, which is a low polar matrix having a 1-octanol/water partition coefficient (logPow) of 4.1 to 4.8.
(5) The matrix as described in (4), wherein a molecular weight of the polyethylene glycol derivative is 60,000 or more.

Advantage of the Invention

The inventors have found that in the case of measurement of a molecular weight of a polyethylene glycol derivative which is a highly polar polymer by the MALDI mass spectrometry, when the polyethylene glycol derivative has a high molecular weight of 40,000 or more, degradation of the polymer is suppressed and a sufficient signal intensity can be obtained by using the low polar matrix as described above to complete the invention.

By using the MALDI mass spectrometry according to the invention, degradation of a polyethylene glycol derivative having a high molecular weight is suppressed and a high signal intensity can be obtained so that the MALDI mass spectrometry according to the invention is extremely useful for industry because it can be suitably used for development and quality control.

In addition, prior to the invention, it has been recommended to use a highly polar matrix, for example, α-cyano-4-hydroxycinnamic acid (CHCA) or 2,5-dihydroxybenzoic acid (DHB) for the measurement of a highly polar polymer, for example, polyethylene glycol (PEG) and it has been reported that better analysis results are obtained by using the highly polar polymer.

MODE FOR CARRYING OUT THE INVENTION

The invention will be described in detail hereinafter.

The polyethylene glycol derivative as the analysis object in the invention may be straight-chain or branched. According to the analysis method of the invention, unlike conventional MALDI mass spectrometry, since, in particular, even in the case of a polyethylene glycol derivative having a branched structure, the degradation thereof is suppressed and the molecular weight thereof can be measured, it is preferred for a polyethylene glycol derivative to have a branched structure and two or more polyethylene glycol chains. There is no upper limit of the number of polyethylene glycol chains and, for example, it is possible to perform the analysis even when the polyethylene glycol derivative has at most 8 polyethylene glycol chains. More typically, a number of the polyethylene glycol chains in the polyethylene glycol derivative is 2, 3, 4, 6 or 8.

The molecular weight of the polyethylene glycol derivative is 40,000 or more. Also, the molecular weight of the polyethylene glycol derivative may be 60,000 or more. Further, the molecular weight of the polyethylene glycol derivative is preferably 1,000,000 or less, and more preferably 200,000 or less. According to the analysis method of the invention, unlike the conventional measuring method using a highly polar matrix, it is possible to analyze with high accuracy even in the case of the polyethylene glycol derivative having a high molecular weight.

In the case of the polyethylene glycol derivative having a molecular weight of 40,000 or more, as opposed to the description of the prior art, the signal intensity was reduced when a highly polar matrix was used.

The polyethylene glycol derivative as the analysis object in the invention is preferably represented by formulae (1) and (2).

In the formulae, Z is a residue obtained by eliminating all hydroxyl groups from a compound having from 2 to 8 hydroxyl groups.

$OA^1$, $OA^2$ and $OA^3$ are each an oxyethylene group, and a, b and c are each from 0 to 5,000 (preferably from 0 to 3,000, and more preferably from 0 to 1,000).

$L^1$, $L^2$ and $L^3$ are each independently an alkylene group which may have an ester bond, a urethane bond, an amide bond, a urea bond, an ether bond or a thioether bond in the alkylene chain or at a terminal. $L^1$, $L^2$ and $L^3$ may be the same or different from each other in one molecule.

p, q and r are each independently 0 or 1.

s and t are each independently from 0 to 8 (particularly preferably 2, 3, 4, 6 or 8).

$X^1$, $X^2$ and $X^3$ each independently represent a hydroxyl group, an alkoxy group, for example, a methoxy group, a tert-butyl group or a benzyloxy group, or an active group capable of specifically reacting with a biologically active substance, for example, a protein, a polypeptide or a drug. $X^1$, $X^2$ and $X^3$ may be the same or different from each other in one molecule.

The active group specifically includes, for example, an aldehyde group, an acetal group, a nitrophenyl carbonate group, a succinimidyl carbonate group, a succinimidyl ester group, a mercapto group, a maleimide group, an alkenyl group, an alkynyl group, an azido group, an amino group and a carboxyl group, and preferably includes, for example, an aldehyde group, a nitrophenyl carbonate group, a succinimidyl carbonate group, a succinimidyl ester group, a mercapto group, a maleimide group, an alkynyl group, an azido group, an amino group and a carboxyl group.

The low polar matrix for MALDI mass spectrometry which can be used in the invention is a low polar matrix having a 1-octanol/water partition coefficient from 4.1 to 4.8 (more preferably from 4.3 to 4.8). The 1-octanol/water partition coefficient of the matrix is a numerical value measured by the high-performance liquid chromatography method described in OECD Test Guideline 117.

As the low polar matrix used in the invention, an aromatic compound constituting from 3 elements of carbon, hydrogen and nitrogen may be used. Particularly preferably, trans-2-[3-(4-tert-butylphenyl)-2-methyl-2-propenylidene]malononitrile is exemplified.

The ratio of the polyethylene glycol derivative to the matrix for MALDI mass spectrometry is not particularly limited. The ratio of polyethylene glycol derivative:matrix for MALDI mass spectrometry is preferably from 1:100 (molar ratio) to 1:1,000,000 (molar ratio), and more preferably from 1:500 (molar ratio) to 1:100,000 (molar ratio).

In the preparation method of sample for analysis of the invention, as the solvent which can be used to produce a liquid containing the matrix for MALDI mass spectrometry and the polyethylene glycol derivative, a solvent which can dissolve the matrix for MALDI mass spectrometry and the polyethylene glycol derivative is desirable. Specifically, the solvent includes, for example, tetrahydrofuran, methanol, ethanol, n-propyl alcohol, isopropyl alcohol, hexafluoroisopropyl alcohol, acetone, methyl ethyl ketone, acetonitrile, ethyl acetate, methylene chloride, chloroform and carbon tetrachloride. In addition, the solvents may be used individually or as a mixture of two or more kinds. The concentration when the matrix for MALDI mass spectrometry or the polyethylene glycol derivative is dissolved in the solvent is preferably from 1 to 100 mg/mL.

The matrix for MALDI mass spectrometry may contain an ionizing agent. The ionizing agent specifically includes, for example, a metal salt, an ammonium salt and an organic salt, for example, sodium trifluoroacetate, silver trifluoroacetate, copper nitrate, sodium chloride and potassium chloride.

As to the ratio of the ionizing agent contained to the matrix for MALDI mass spectrometry, the ratio of the ionizing agent:matrix for MALDI mass spectroscopy is preferably from 1:1 (molar ratio) to 1:10,000 (molar ratio), and more preferably from 1:10 (molar ratio) 1:5,000 (molar ratio).

After dissolving the ionizing agent in a solvent, the matrix for MALDI mass spectrometry may be mixed, and in this case, the concentration of the ionizing agent dissolved in the solvent is preferably approximately from 0.1 to 100 mg/mL.

The sample for MALDI mass spectrometry thus prepared by the preparation method of sample for analysis of the invention provides a high signal intensity even when the laser intensity is decreased. Therefore, since the MALDI mass spectrometry which is performed by using the sample for MALDI mass spectrometry prepared by the preparation method of sample for analysis of the invention suppresses the degradation of polymer and can measure the accurate molecular weight, it can be suitably used for quality control of the polyethylene glycol derivative.

EXAMPLES

The invention will be described in more detail with reference to the examples.

Example 1

Trans-2-[3-(4-tert-butylphenyl)-2-methyl-2-propenylidene]malononitrile (Santa Cruz Co., purity of 99% or more, 1-octanol/water partition coefficient of 4.6) was used as a matrix for MALDI mass spectrometry, a branched polyethylene glycol derivative SUNBRIGHT GL2-600HO (produced by NOF, molecular weight of 60,000, Compound 1 shown below) was used as a sample, and sodium trifluoroacetate was used as an ionizing agent. A tetrahydrofuran solution of the matrix for MALDI mass spectrometry (concentration of 20 mg/mL), a tetrahydrofuran solution of the branched polyethylene glycol derivative (concentration of 60 mg/mL) and a tetrahydrofuran solution of sodium trifluoroacetate (ionizing agent) (concentration of 2 mg/mL) were mixed in 100:1:2 (volume ratio).

1 µL of the mixed solution of the matrix for MALDI mass spectrometry, the branched polyethylene glycol derivative and the ionizing agent was dropped with a micropipette on a target for MALDI mass spectrometry and dried. The target was inserted into a MALDI mass spectrometer of AutoFlex III Model, produced by Bruker Daltonics Inc. Then, the measurement was performed at an acceleration voltage of 20.0 kV in a positive ionization mode of 2,500 laser shots integration with appropriate adjustment of laser intensity. Evaluation of signal intensity was decided to use a signal intensity of a peak top in the mass spectrum obtained.

Figure 1:
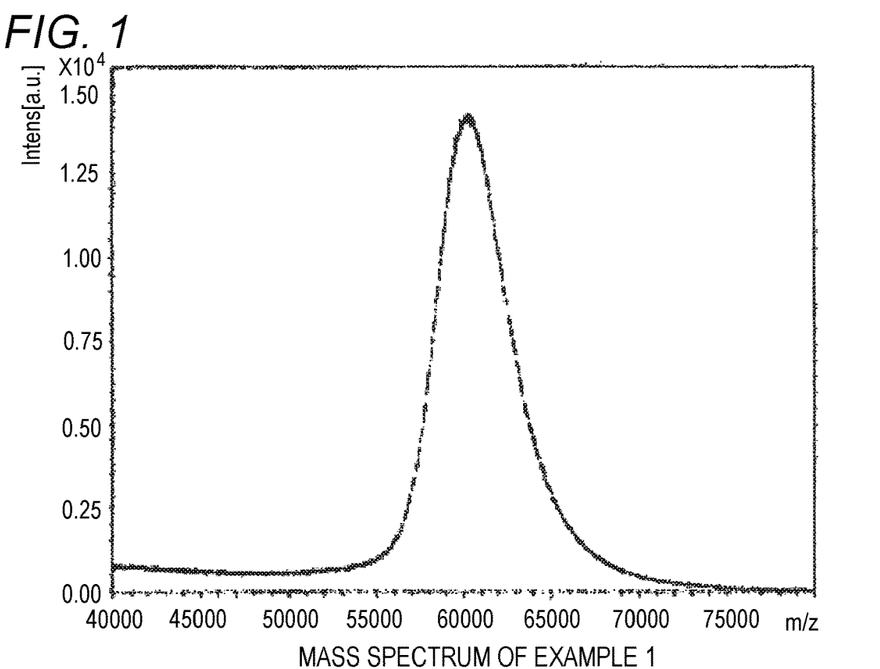
FIG. 1 is a chart showing the mass spectrum obtained in Example 1.

The signal intensity in the case of using the preparation method of the sample for MALDI mass spectrometry of Example 1 was 10,389 counts. The mass spectrum chart obtained in Example 1 is shown in FIG. 1.

Compound 1

Comparative Example 1-1

Figure 2:
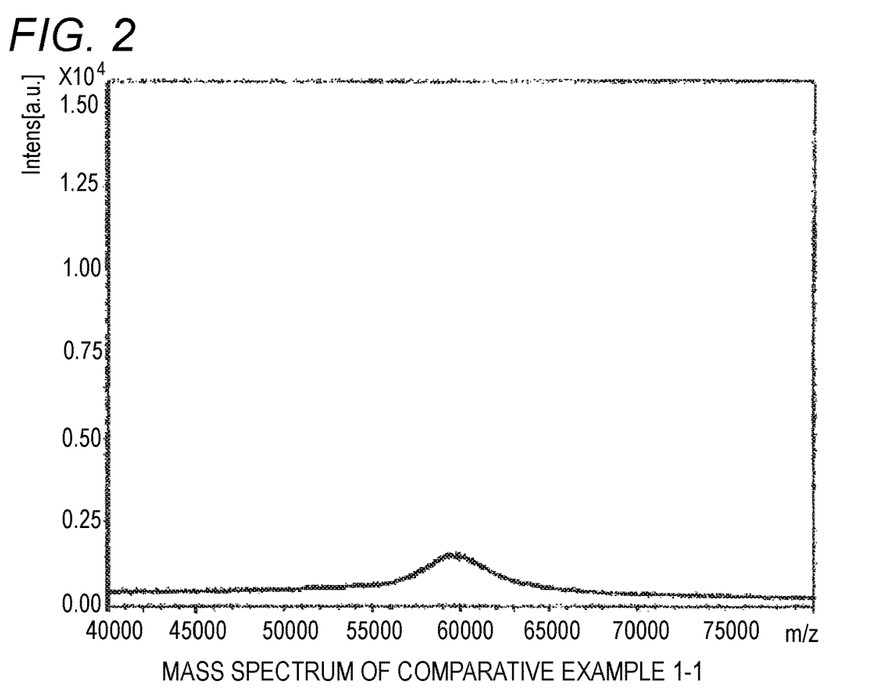
FIG. 2 is a chart showing the mass spectrum obtained in Comparative Example 1-1.

The measurement and evaluation were performed under the same conditions as in Example 1 except for using α-cyano-4-hydroxycinnamic acid (CHCA, 1-octanol/water partition coefficient of 0.9) as the matrix. The signal intensity in the case of using the preparation method of the sample for MALDI mass spectrometry of Comparative Example 1-1 was 978 counts. The mass spectrum chart obtained in Comparative Example 1-1 is shown in FIG. 2.

Comparative Example 1-2

Figure 3:
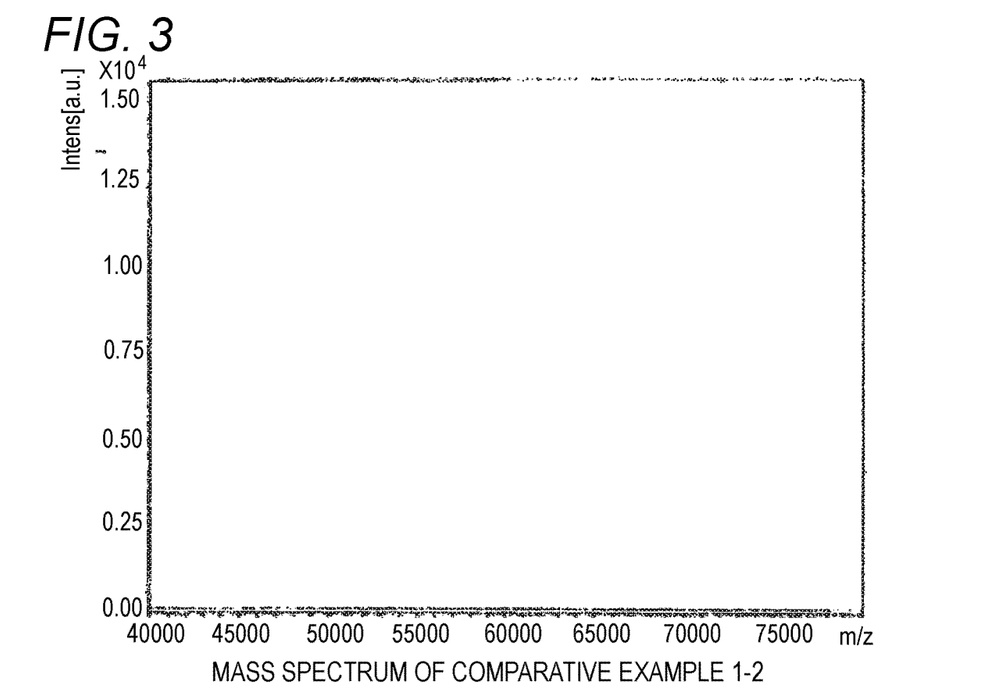
FIG. 3 is a chart showing the mass spectrum obtained in Comparative Example 1-2.

The measurement and evaluation were performed under the same conditions as in Example 1 except for using 2,5-dihydroxybenzoic acid (DHB, 1-octanol/water partition coefficient of 0.6) as the matrix. In the case of using the preparation method of the sample for MALDI mass spectrometry of Comparative Example 1-2, the signal was not detected. The mass spectrum chart obtained in Comparative Example 1-2 is shown in FIG. 3.

TABLE 1

|  | Signal Intensity |
| --- | --- |
| Example 1 | 10,389 |
| Comparative Example 1-1 | 978 |
| Comparative Example 1-2 | 0 |

Example 2

Figure 4:
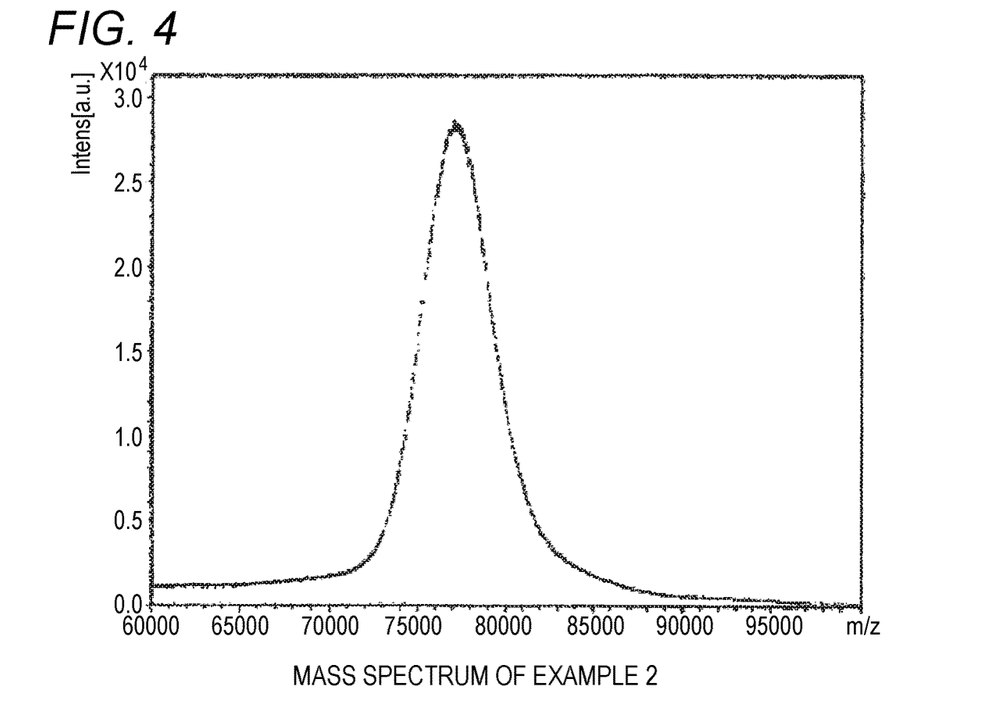
FIG. 4 is a chart showing the mass spectrum obtained in Example 2.

The measurement and evaluation were performed under the same conditions as in Example 1 except for using a tetrahydrofuran solution of SUNBRIGHT GL4-800HO (produced by NOF, molecular weight of 80,000, Compound 2 shown below) at concentration of 80 mg/mL. The signal intensity in the case of using the preparation method of the sample for MALDI mass spectrometry of Example 2 was 23,734 counts. The mass spectrum chart obtained in Example 2 is shown in FIG. 4.

Compound 2

Comparative Example 2-1

Figure 5:
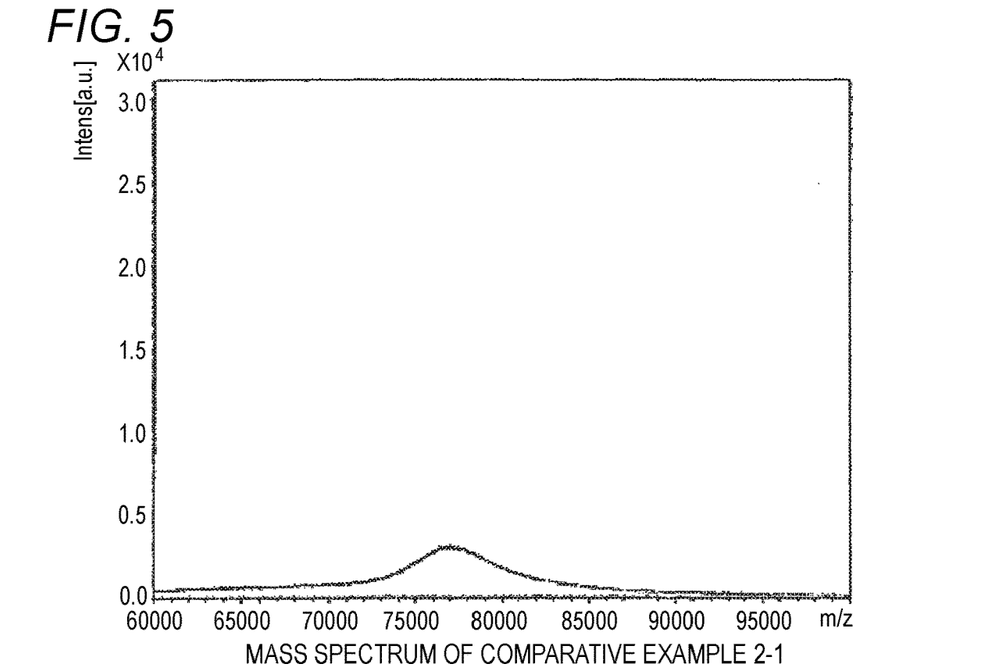
FIG. 5 is a chart showing the mass spectrum obtained in Comparative Example 2-1.

The measurement and evaluation were performed under the same conditions as in Example 2 except for using CHCA as the matrix. The signal intensity in the case of using the preparation method of the sample for MALDI mass spectrometry of Comparative Example 2-1 was 2,005 counts. The mass spectrum chart obtained in Comparative Example 2-1 is shown in FIG. 5.

Comparative Example 2-2

Figure 6:
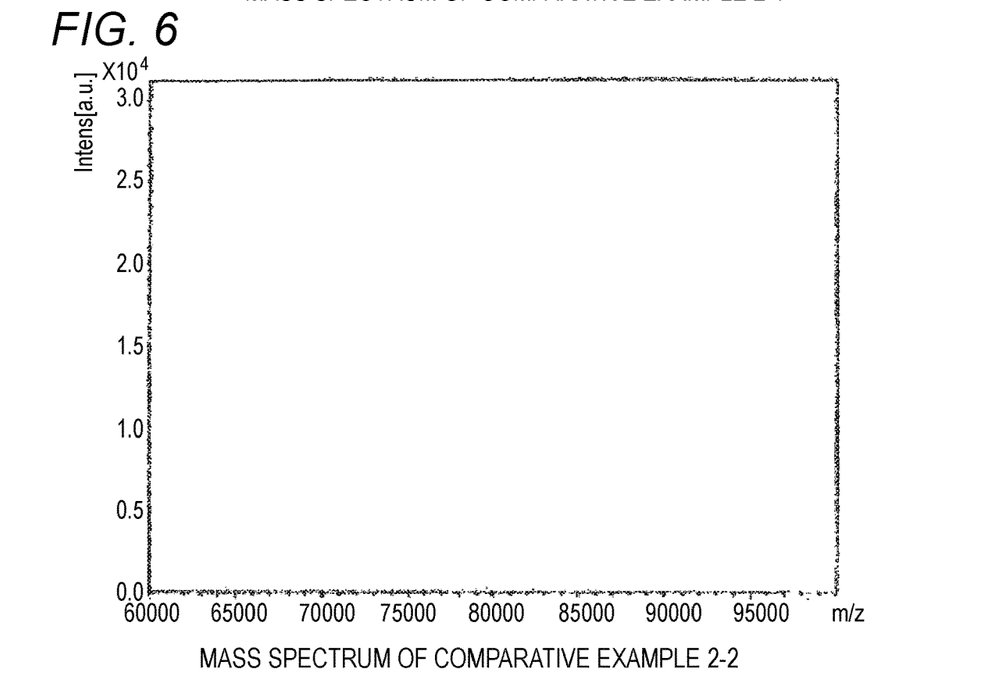
FIG. 6 is a chart showing the mass spectrum obtained in Comparative Example 2-2.

The measurement and evaluation were performed under the same conditions as in Example 2 except for using DHB as the matrix. In the case of using the preparation method of the sample for MALDI mass spectrometry of Comparative Example 2-2, the signal was not detected. The mass spectrum chart obtained in Comparative Example 2-2 is shown in FIG. 6.

TABLE 2

|  | Signal Intensity |
| --- | --- |
| Example 2 | 23,734 |
| Comparative Example 2-1 | 2,005 |
| Comparative Example 2-2 | 0 |

Example 3

Figure 7:
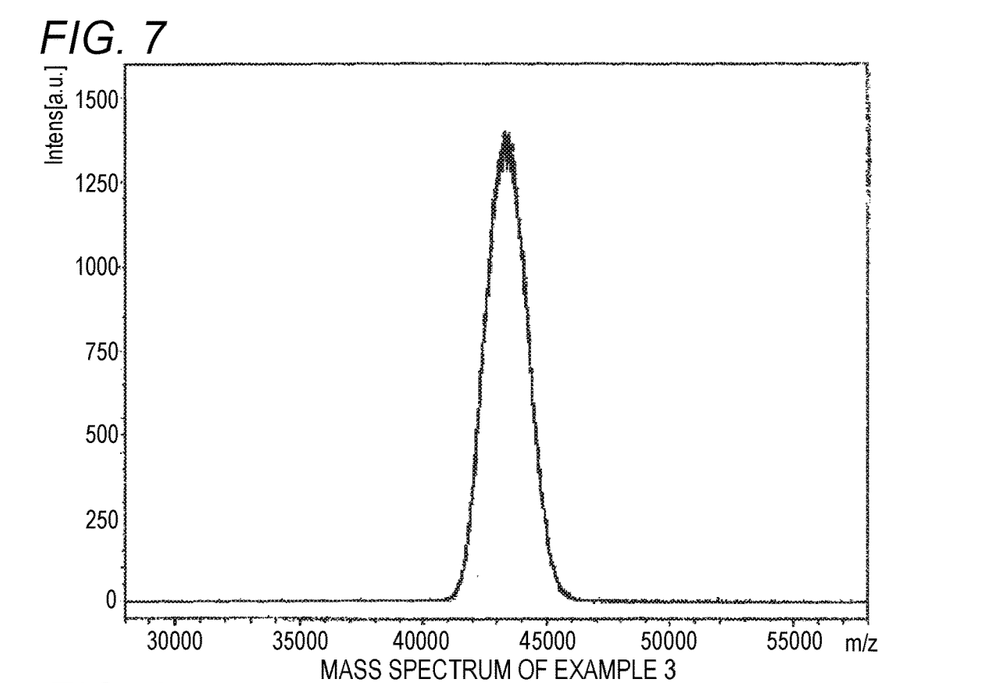
FIG. 7 is a chart showing the mass spectrum obtained in Example 3.

The measurement and evaluation were performed under the same conditions as in Example 1 except for using a tetrahydrofuran solution of SUNBRIGHT MEH-40T (produced by NOF, molecular weight of 40,000, Compound 4 shown below) at concentration of 40 mg/mL. The signal intensity in the case of using the preparation method of the sample for MALDI mass spectrometry of Example 3 was 1,390 counts. The mass spectrum chart obtained in Example 3 is shown in FIG. 7.

H—(OCH$_2$CH$_2$)$_{908}$—OMe      Compound 4

Comparative Example 3-1

Figure 8:
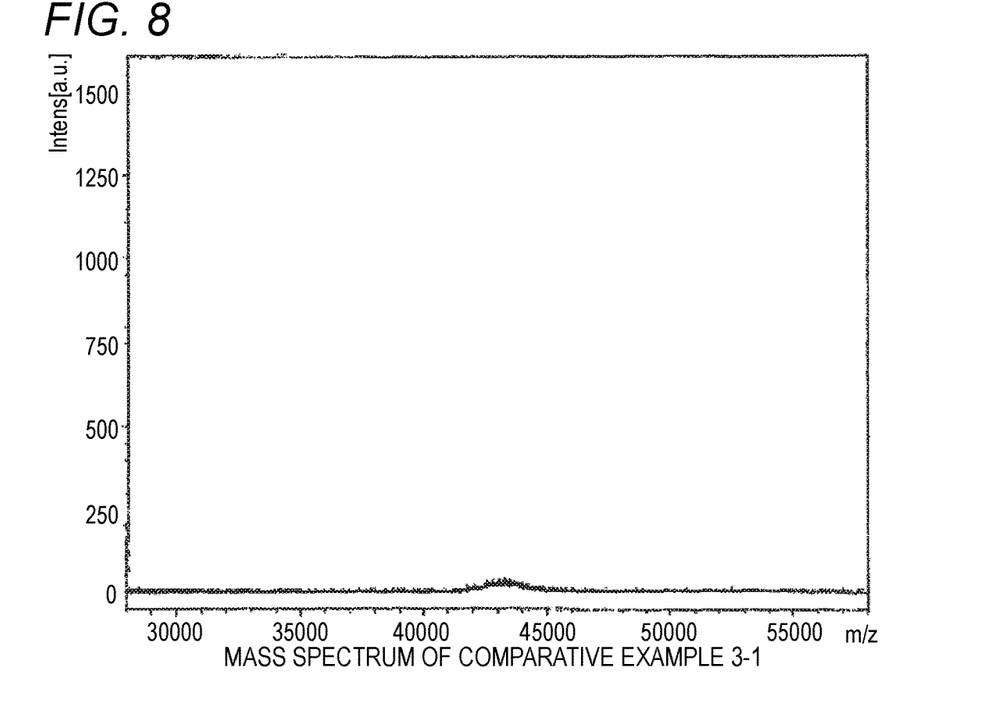
FIG. 8 is a chart showing the mass spectrum obtained in Comparative Example 3-1.

The measurement and evaluation were performed under the same conditions as in Example 3 except for using CHCA as the matrix. The signal intensity in the case of using the preparation method of the sample for MALDI mass spectrometry of Comparative Example 3-1 was 39 counts. The mass spectrum chart obtained in Comparative Example 3-1 is shown in FIG. 8.

Comparative Example 3-2

Figure 9:
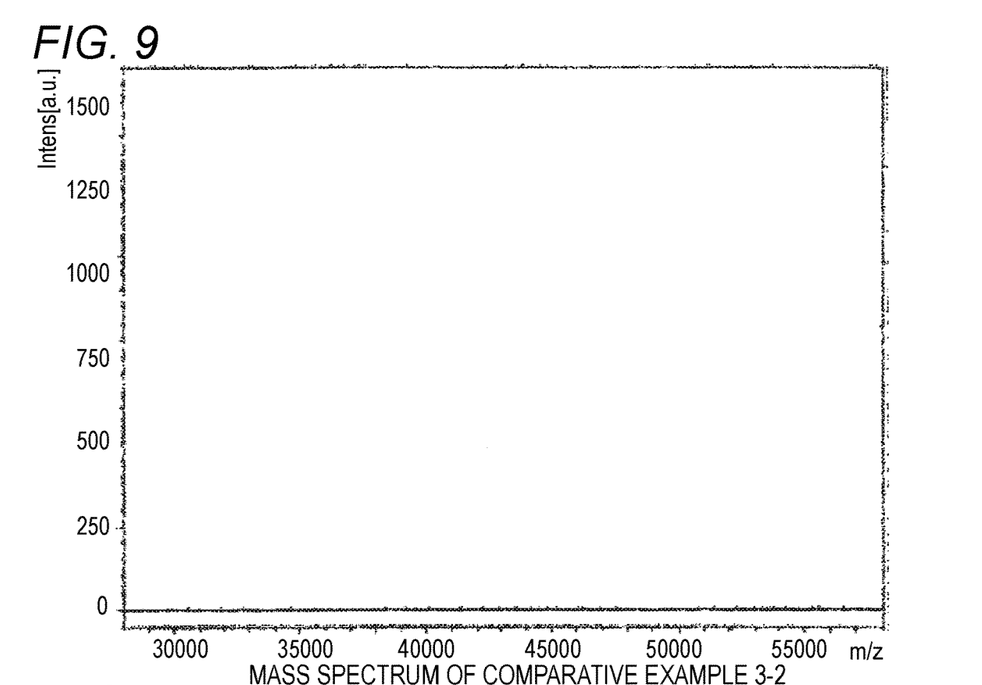
FIG. 9 is a chart showing the mass spectrum obtained in Comparative Example 3-2.

The measurement and evaluation were performed under the same conditions as in Example 3 except for using DHB as the matrix. In the case of using the preparation method of the sample for MALDI mass spectrometry of Comparative Example 3-2, the signal was not detected. The mass spectrum chart obtained in Comparative Example 3-2 is shown in FIG. 9.

TABLE 3

|  | Signal Intensity |
| --- | --- |
| Example 3 | 1,390 |
| Comparative Example 3-1 | 39 |
| Comparative Example 3-2 | 0 |

Example 4

Figure 10:
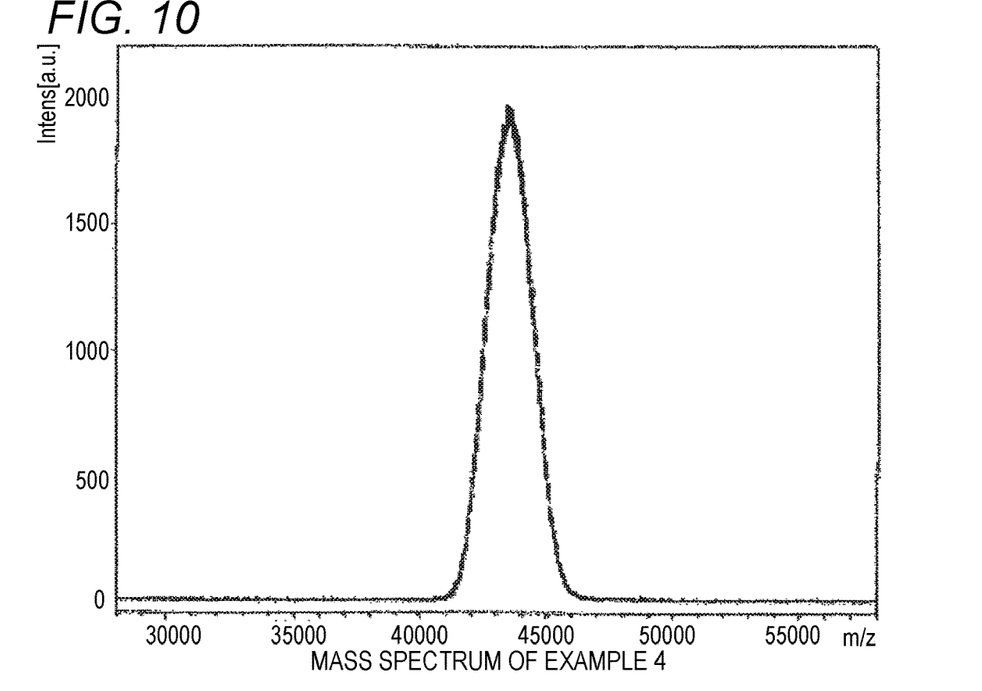
FIG. 10 is a chart showing the mass spectrum obtained in Example 4.

The measurement and evaluation were performed under the same conditions as in Example 1 except for using a tetrahydrofuran solution of SUNBRIGHT ME-400GS (produced by NOF, molecular weight of 40,000, Compound 5 shown below) at concentration of 40 mg/mL. The signal intensity in the case of using the preparation method of the sample for MALDI mass spectrometry of Example 4 was 1,971 counts. The mass spectrum chart obtained in Example 4 is shown in FIG. 10.

Compound 5

Comparative Example 4-1

Figure 11:
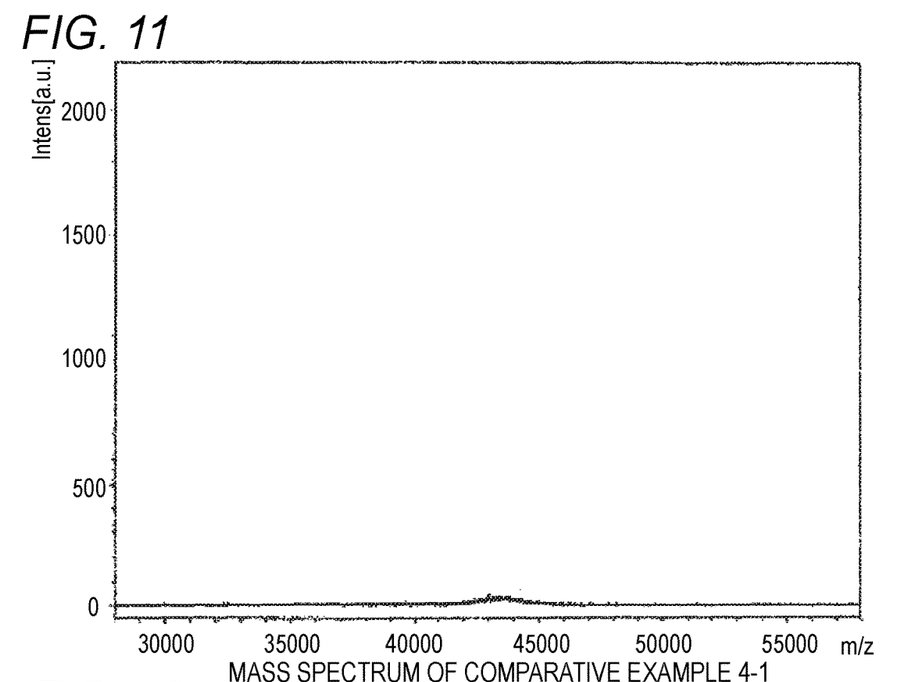
FIG. 11 is a chart showing the mass spectrum obtained in Comparative Example 4-1.

The measurement and evaluation were performed under the same conditions as in Example 4 except for using CHCA as the matrix. The signal intensity in the case of using the preparation method of the sample for MALDI mass spectrometry of Comparative Example 4-1 was 39 counts. The mass spectrum chart obtained in Comparative Example 4-1 is shown in FIG. 11.

Comparative Example 4-2

Figure 12:
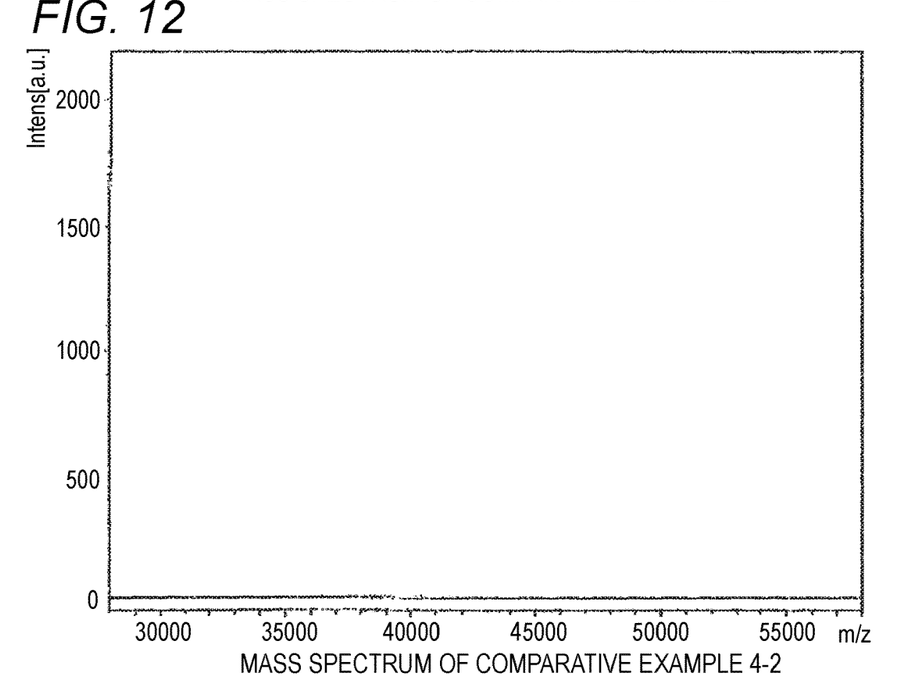
FIG. 12 is a chart showing the mass spectrum obtained in Comparative Example 4-2.

The measurement and evaluation were performed under the same conditions as in Example 4 except for using DHB as the matrix. In the case of using the preparation method of the sample for MALDI mass spectrometry of Comparative Example 4-2, the signal was not detected. The mass spectrum chart obtained in Comparative Example 4-2 is shown in FIG. 12.

TABLE 4

| | Signal Intensity |
|---|---|
| Example 4 | 1,971 |
| Comparative Example 4-1 | 39 |
| Comparative Example 4-2 | 0 |

Example 5

Figure 13:
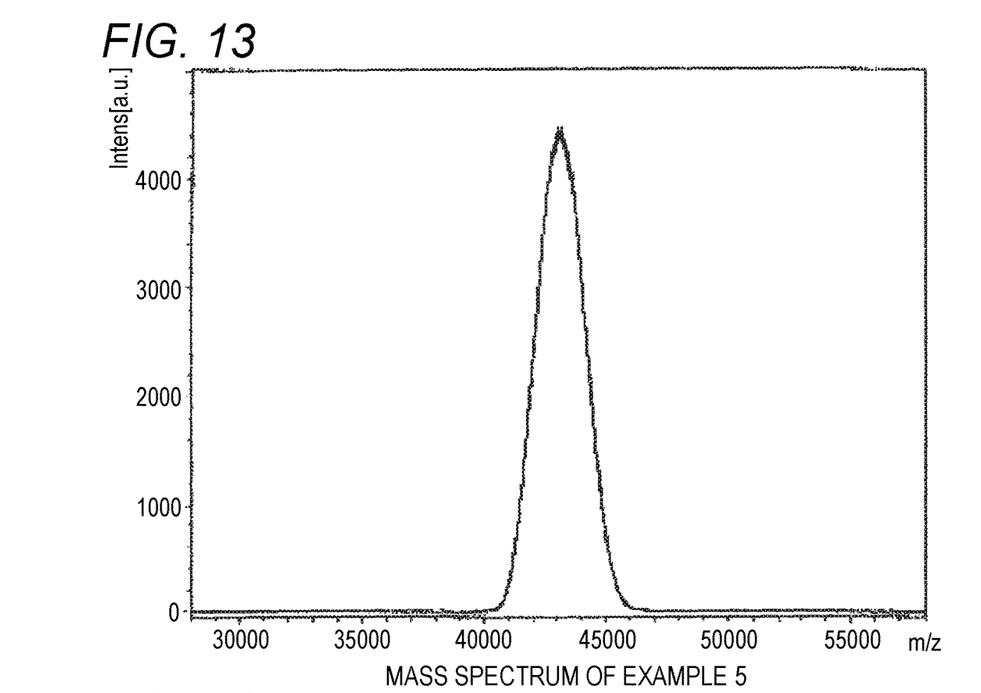
FIG. 13 is a chart showing the mass spectrum obtained in Example 5.

The measurement and evaluation were performed under the same conditions as in Example 1 except for using a tetrahydrofuran solution of SUNBRIGHT GL2-400HO (produced by NOF, molecular weight of 40,000, Compound 6 shown below) at concentration of 40 mg/mL. The signal intensity in the case of using the preparation method of the sample for MALDI mass spectrometry of Example 5 was 4,469 counts. The mass spectrum chart obtained in Example 5 is shown in FIG. 13.

Compound 6

Comparative Example 5-1

Figure 14:
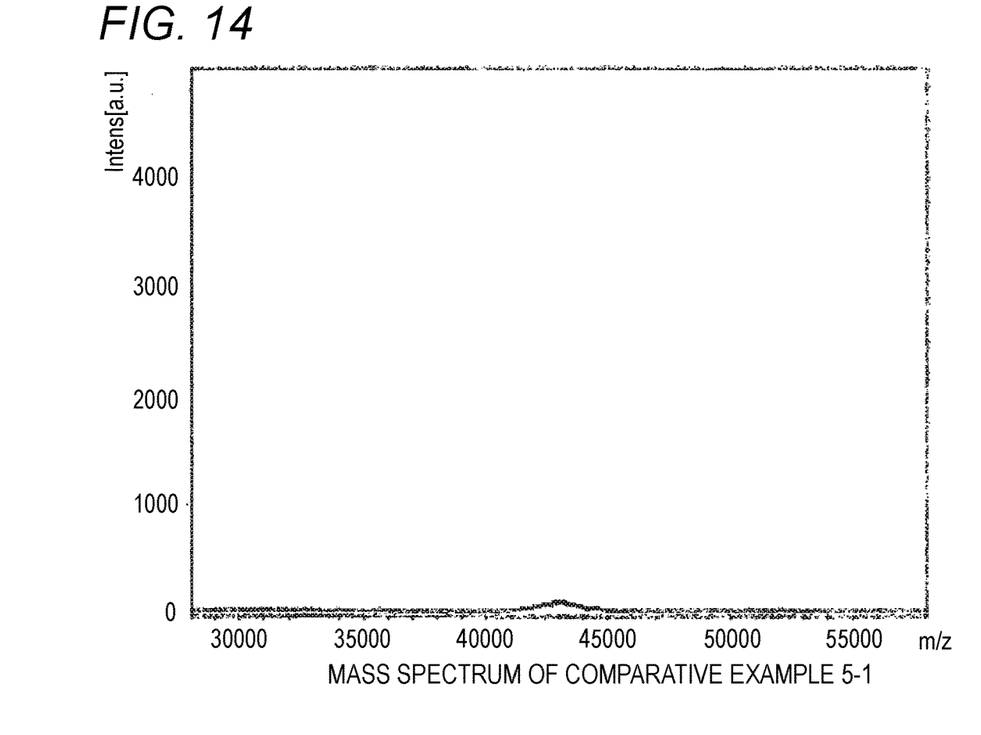
FIG. 14 is a chart showing the mass spectrum obtained in Comparative Example 5-1.

The measurement and evaluation were performed under the same conditions as in Example 5 except for using CHCA as the matrix. The signal intensity in the case of using the preparation method of the sample for MALDI mass spectrometry of Comparative Example 5-1 was 85 counts. The mass spectrum chart obtained in Comparative Example 5-1 is shown in FIG. 14.

Comparative Example 5-2

Figure 15:
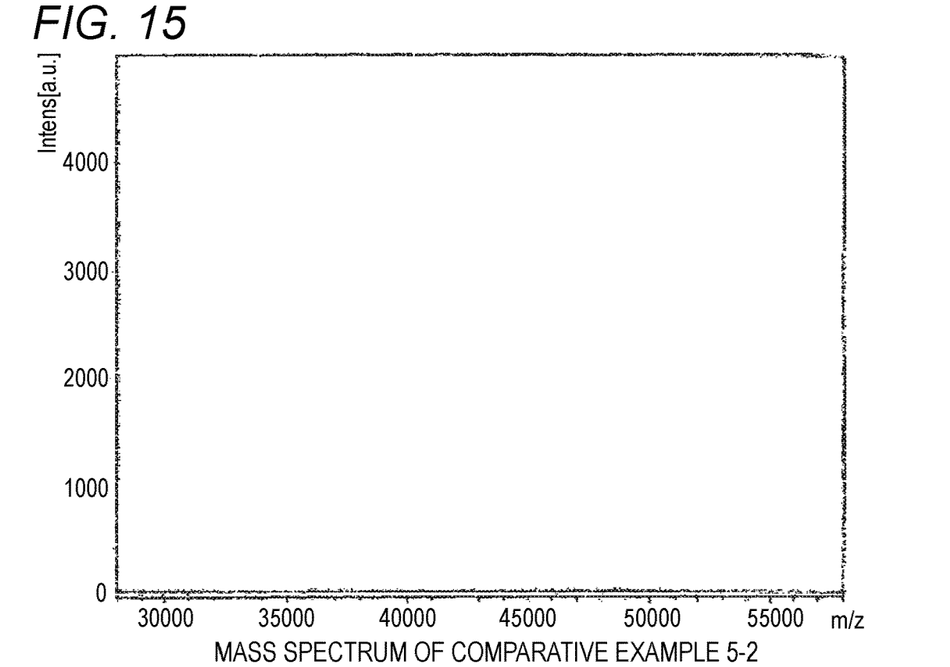
FIG. 15 is a chart showing the mass spectrum obtained in Comparative Example 5-2.

The measurement and evaluation were performed under the same conditions as in Example 5 except for using DHB as the matrix. In the case of using the preparation method of the sample for MALDI mass spectrometry of Comparative Example 5-2, the signal was not detected. The mass spectrum chart obtained in Comparative Example 5-2 is shown in FIG. 15.

TABLE 5

| | Signal Intensity |
|---|---|
| Example 5 | 4,469 |
| Comparative Example 5-1 | 85 |
| Comparative Example 5-2 | 0 |

Example 6

Figure 16:
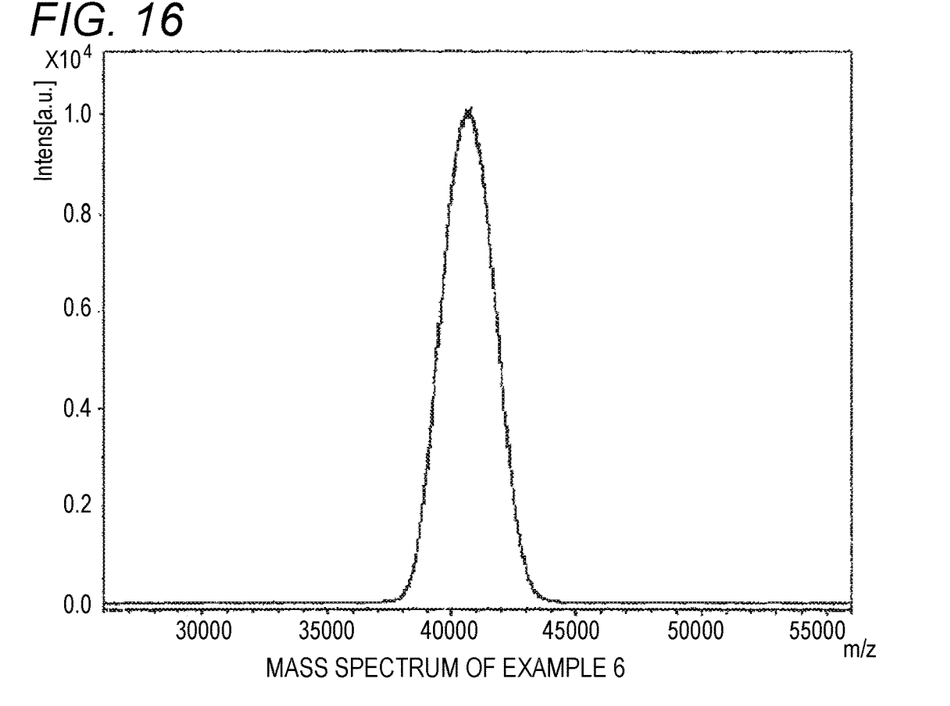
FIG. 16 is a chart showing the mass spectrum obtained in Example 6.

The measurement and evaluation were performed under the same conditions as in Example 1 except for using a tetrahydrofuran solution of SUNBRIGHT PTE-40000 (produced by NOF, molecular weight of 40,000, Compound 7 shown below) at concentration of 40 mg/mL. The signal intensity in the case of using the preparation method of the sample for MALDI mass spectrometry of Example 6 was 10,138 counts. The mass spectrum chart obtained in Example 6 is shown in FIG. 16.

Compound 7

Comparative Example 6-1

Figure 17:
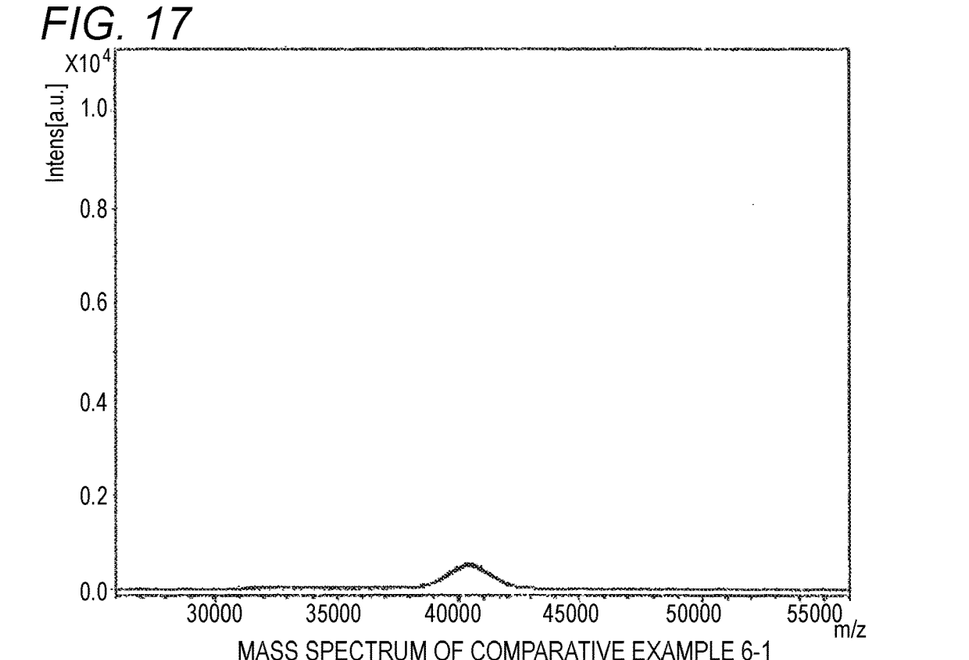
FIG. 17 is a chart showing the mass spectrum obtained in Comparative Example 6-1.

The measurement and evaluation were performed under the same conditions as in Example 6 except for using CHCA as the matrix. The signal intensity in the case of using the preparation method of the sample for MALDI mass spectrometry of Comparative Example 6-1 was 564 counts. The mass spectrum chart obtained in Comparative Example 6-1 is shown in FIG. 17.

Comparative Example 6-2

Figure 18:
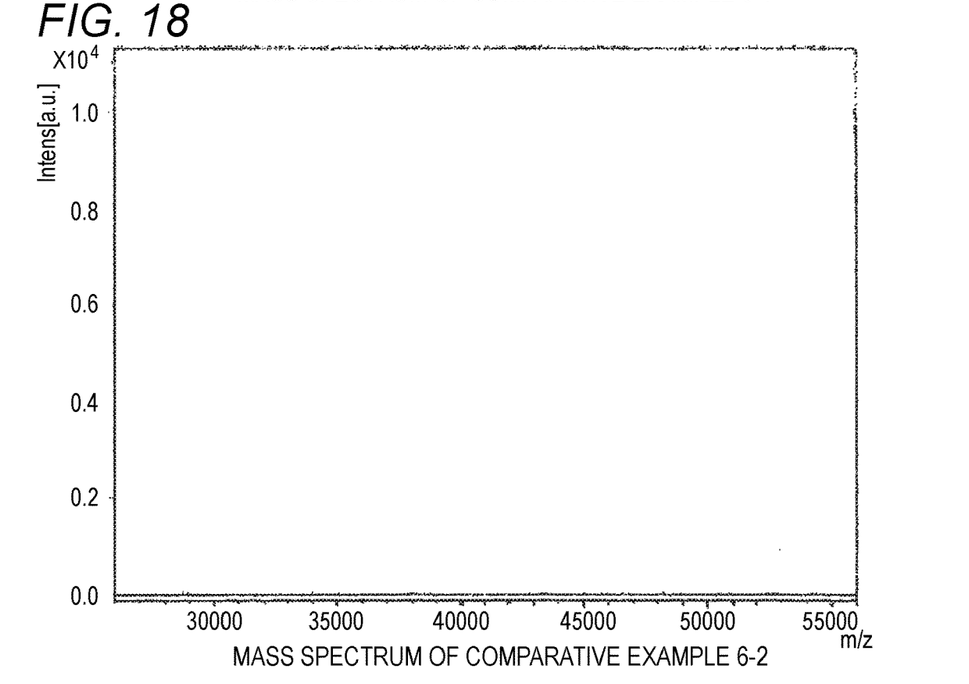
FIG. 18 is a chart showing the mass spectrum obtained in Comparative Example 6-2.

The measurement and evaluation were performed under the same conditions as in Example 6 except for using DHB as the matrix. In the case of using the preparation method of the sample for MALDI mass spectrometry of Comparative Example 6-2, the signal was not detected. The mass spectrum chart obtained in Comparative Example 6-2 is shown in FIG. 18.

TABLE 6

| | Signal Intensity |
|---|---|
| Example 6 | 10,138 |
| Comparative Example 6-1 | 564 |
| Comparative Example 6-2 | 0 |

While the invention has been described in detail and with reference to specific embodiments thereof, it will be apparent to those skilled in the art that various changes and modifications can be made therein without departing from the spirit and scope of the invention.

This application is based on a Japanese patent application filed on Mar. 31, 2015 (Japanese Patent Application No. 2015-071739), and the whole contents thereof are incorporated herein by reference. Also, all the references cited herein are incorporated as a whole.

The invention clamed is:

1. An analytical method of measuring a molecular weight of a polyethylene glycol derivative having a molecular weight of 40,000 or more using a matrix-assisted laser desorption mass spectrometry technique, which method comprises irradiating a mixture comprising the polyethylene glycol derivative and a matrix with a laser beam to vaporize the polyethylene glycol derivative together with the matrix, thereby measuring a molecular weight of the polyethylene glycol derivative, wherein the matrix is a low polar matrix having a 1-octanol/water partition coefficient (logPow) of 4.1 to 4.8, and the polyethylene glycol derivative is represented by formulae (1) and (2):

(1)

(2)

$$A = \text{---}X^2 \quad \text{or} \quad \begin{array}{c} CH_2\text{---}(OA^3)_c\text{---}(L^3)_r\text{---}X^3 \\ | \\ CH\text{---}(OA^3)_c\text{---}(L^3)_r\text{---}X^3, \\ | \\ \text{---}OCH_2 \end{array}$$

wherein Z represents a residue obtained by eliminating all hydroxyl groups from a compound having from 3 to 8 hydroxyl groups;

$OA^1$, $OA^2$ and $OA^3$ are each independently an oxyethylene group;

$L^1$, $L^2$ and $L^3$ are each independently an alkylene group which may have an ester bond, a urethane bond, an amide bond, a urea bond, an ether bond or a thioether bond in the alkylene chain or at a terminal, $L^1$, $L^2$ and $L^3$ may be the same or different from each other in one molecule;

$X^1$, $X^2$ and $X^3$ are each independently a hydroxyl group, an alkoxy group, a tert-butyl group or a benzyloxy group, or an active group capable of specifically reacting with a biologically active substance, $X^1$, $X^2$ and $X^3$ may be the same or different from each other in one molecule;

a, b and c are each independently from 0 to 5,000;

p, q and r are each independently 0 or 1, and s and t are each independently from 0 to 8.

2. The analytical method as claimed in claim 1, wherein a molecular weight of the polyethylene glycol derivative is 60,000 or more.

3. The analytical method as claimed in claim 2, wherein the matrix is trans-2-[3-(4-tert-butylphenyl)-2-methyl-2-propenylidene]malononitrile.

4. The analytical method as claimed in claim 1, wherein the matrix is trans-2-[3-(4-tert-butylphenyl)-2-methyl-2-propenylidene]malononitrile.

5. A composition comprising a matrix and a polyethylene glycol derivative having a molecular weight of 40,000 or more, wherein the matrix is for use in a matrix-assisted laser desorption mass spectrometry of the polyethylene glycol derivative and is a low polar matrix having a 1-octanol/water partition coefficient (logPow) of 4.1 to 4.8, and the polyethylene glycol derivative is represented by formulae (1) and (2):

(1)

(2)

$$A = \text{---}X^2 \quad \text{or} \quad \begin{array}{c} CH_2\text{---}(OA^3)_c\text{---}(L^3)_r\text{---}X^3 \\ | \\ CH\text{---}(OA^3)_c\text{---}(L^3)_r\text{---}X^3, \\ | \\ \text{---}OCH_2 \end{array}$$

wherein Z represents a residue obtained by eliminating all hydroxyl groups from a compound having from 3 to 8 hydroxyl groups;

$OA^1$, $OA^2$ and $OA^3$ are each independently an oxyethylene group;

$L^1$, $L^2$ and $L^3$ are each independently an alkylene group which may have an ester bond, a urethane bond, an amide bond, a urea bond, an ether bond or a thioether bond in the alkylene chain or at a terminal, $L^1$, $L^2$ and $L^3$ may be the same or different from each other in one molecule;

$X^1$, $X^2$ and $X^3$ are each independently a hydroxyl group, an alkoxy group, a tert-butyl group or a benzyloxy group, or an active group capable of specifically reacting with a biologically active substance, $X^1$, $X^2$ and $X^3$ may be the same or different from each other in one molecule;

a, b and c are each independently from 0 to 5,000;

p, q and r are each independently 0 or 1, and s and t are each independently from 0 to 8.

6. The composition as claimed in claim 5, wherein a molecular weight of the polyethylene glycol derivative is 60,000 or more.

* * * * *